J. C. MIKKELSEN
BEGONIA PLANT
Filed Aug. 19, 1974
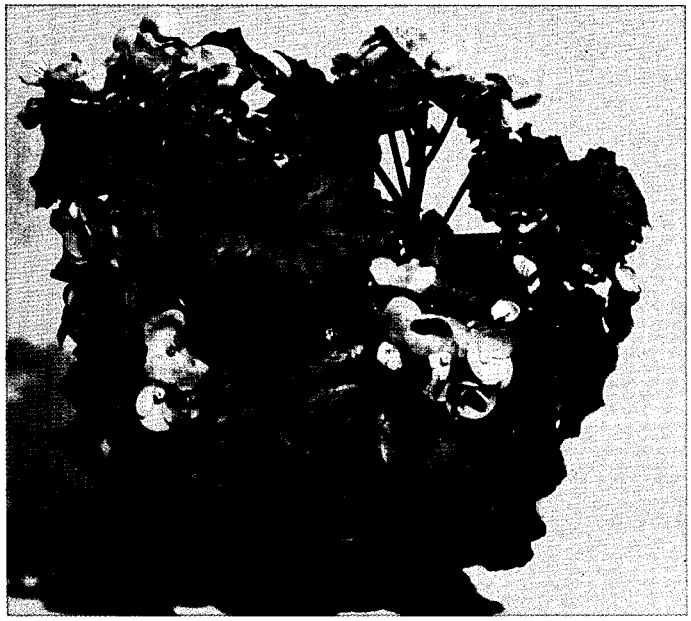

United States Patent

Plant Pat. 3,786
Patented Sept. 23, 1975

3,786

BEGONIA PLANT

James C. Mikkelsen, Ashtabula, Ohio, assignor to Mikkelsens Inc., Ashtabula, Ohio Filed Aug. 19, 1974, Ser. No. 498,867
Int. Cl. A01h 5/00
U.S. Cl. Plt.—68 1 Claim The present invention relates to a new and distinctive variety of begonia plant, know by the varietal name Improved Krefeld Orange and botanically known as *Begonia elatior,* (B × *hiemalis*-Fotsch). The new cultivar was discovered as a mutation of the parent cultivar Krefeld Orange, disclosed in U.S. Plant Pat. 3,403, issued Sept. 18, 1973, to Siegfried Merholz, with the new cultivar being noted in a propagation bed of small plants from leaf cuttings of the parent cultivar. Asexual reproduction by stem and leaf cuttings has reproduced the unique features of the new variety through successive propagations.

The following characteristics distinguish the new begonia from both its parent and other begonias commercially known and used in the floriculture industry:

1. The plum red color of the foliage.
2. Deeper orange/red flower color.
3. Tepals of the flowers have a sparkling velvety lustre.
4. Plant stems and flower stems are deep blood red in color.
5. Propagation by leaf cuttings is consistently excellent. Very few leaf cuttings fail to produce adventitious buds.
6. Plant growth is somewhat reduced during low light periods, presumably because of reduced chlorophyll.
7. Spring, summer, and fall growth is less than Schwabenland Red but more than adequate for normal pot plant production.
8. Outdoor planting in comparison to red leaf type fibrous begonias are superior for contrast because foliage color is richer and flower color and size is not available in fibrous rooted begonias. The new cultivar accordingly has excellent potential as an outdoor specimen plant.

The accompanying colored photographic drawing illustrates the new variety, with the color being as true as reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Partage: Mutation of Krefeld Orange.

Propagation: Propagation by leaf cuttings is 5–7 days faster than both the parent variety and Schwabenland Red, with the latter being used as a comparison plant.

Rooting habit: Rooting is accomplished in 20–25 days with propagation media temperatures at 20°–22° C.

Roots are fine, well branched. Adventitious shoots emerge sufficiently in seven to eight weeks for shipping.

Plant form: Upright—bushy.

Habit of growth: Upright, with very little self-branching; average internodes with rate of growth slower than green leaf begonias.

Blooming habits: Can be partially controlled by temperature, daylength, and nutrition. Once plant has initiated flower, the response is continuous for as much as six months.

Blooming season: Normal blooming season is November. However, leaf propagation and modern plant management allows the new begonia to be produced year round.

Foliage: Heart shaped, without deep sinuses; some serration; is seldom flat but irregularly wavy, sometimes concave other times convex.

*Size.*—Smaller than other Schwabenland begonias, measuring 8–10 cm. in diameter.

*Shape.*—Oval to heart shaped.

*Texture.*—Smooth and waxy.

*Margin.*—Shallow sinuses, some serration.

*Color.*—Best described as plum red, color between purple 187A and 183A. The underside of the leaf is red 181A. Stem, leaf petiole, and flower stem color is close to red 46A.

Disease resistance: More resistant to common mildew than the comparison cultivar Schwabenland Red.

Flowers:

*Borne.*—On strong vertical trusses at slight angles to the stem. Flower placement is symmetrical around the plant.

*Quantity.*—Numbers of flowers are average for this type of begonia.

*Buds.*—Are generally flat until opening. Size is comparable to other Schwabenland begonias.

*Tepals.*—Tepals have a satin feel; inner surface has velvet lustre somewhat darker than red 33A; outer surface is slightly lighter in color.

*Reproductive organs.*—Stamens—Deep yellow—anthers are orange/red 30B. Underside of anthers are red. Pollen—Flat yellow. Styles/ovaries—None seen to date.

I claim:

1. A new and distinct form of begonia characterized particularly as to uniqueness by its deep orange/red flower color, with the tepals having a sparkling velvety lustre; plum red foliage color and deep blood red color of both the plant and flower stems; excellent propagation habit from leaf cuttings, and by its excellent potential as an outdoor specimen plant.

No references cited.

ROBERT E. BAGWILL, Primary Examiner